(12) United States Patent  (10) Patent No.: US 8,007,463 B2
Pudelko et al.                (45) Date of Patent:    Aug. 30, 2011

(54) BI-DIRECTIONAL CATHETER ASSEMBLY AND METHOD THEREFOR

(75) Inventors: Greg Pudelko, Rosesville, MN (US);
Brian Fischer, Minneapolis, MN (US);
Brian Honebrink, Stillwater, MN (US)

(73) Assignee: Greatbatch Ltd., Clarence, NY (US)

( * ) Notice: Subject to any disclaimer, the term of this patent is extended or adjusted under 35 U.S.C. 154(b) by 71 days.

(21) Appl. No.: 12/546,206

(22) Filed: Aug. 24, 2009

(65) Prior Publication Data

US 2009/0312699 A1    Dec. 17, 2009

Related U.S. Application Data

(63) Continuation of application No. 10/670,150, filed on Sep. 24, 2003, now Pat. No. 7,588,555.

(51) Int. Cl.
*A61M 37/00* (2006.01)
(52) U.S. Cl. .................... 604/95.04; 604/528
(58) Field of Classification Search ............ 604/95.04, 604/93.01, 510, 528, 535, 524, 534; 600/585, 600/114, 146
See application file for complete search history.

(56) References Cited

U.S. PATENT DOCUMENTS

| | | | |
|---|---|---|---|
| 4,898,577 A | 2/1990 | Badger et al. | |
| 5,030,204 A * | 7/1991 | Badger et al. | 604/95.04 |
| 5,168,864 A * | 12/1992 | Shockey | 600/144 |
| 5,195,968 A | 3/1993 | Lundquist et al. | |
| 5,358,478 A | 10/1994 | Thompson et al. | |
| 5,545,200 A | 8/1996 | West et al. | |
| 5,588,964 A | 12/1996 | Imran et al. | |
| 5,642,736 A | 7/1997 | Avitall | |
| 5,656,030 A | 8/1997 | Hunjan et al. | |
| 5,807,249 A * | 9/1998 | Qin et al. | 600/374 |
| 5,826,576 A | 10/1998 | West | |
| 5,897,554 A | 4/1999 | Chia et al. | |
| 5,944,690 A | 8/1999 | Falwell et al. | |
| 6,171,277 B1 | 1/2001 | Ponzi et al. | |
| 6,183,463 B1 | 2/2001 | Webster, Jr. | |

(Continued)

FOREIGN PATENT DOCUMENTS

EP      1038545 A2    9/2000
(Continued)

OTHER PUBLICATIONS

"U.S. Appl. No. 10/670,150, Final Office Action mailed Dec. 31, 2007", 6 pgs.

(Continued)

*Primary Examiner* — Laura A Bouchelle
(74) *Attorney, Agent, or Firm* — Michael F. Scalise

(57) ABSTRACT

A catheter assembly includes a catheter body extending from a deflectable distal end to a proximal end, and the catheter body includes an actuator lumen. A housing is engaged to the proximal end of the catheter body. A flexible element extends from the housing through the actuator lumen to the deflectable distal end. The deflectable distal end is deflected by pushing and pulling of the flexible element. An actuator is movably coupled with the housing and connected to the flexible element. A tubular support is engaged around the flexible element and connected to the actuator, the tubular support moves with the actuator, and the tubular support substantially constrains lateral movement of the flexible element. The tubular support is telescopically received and engaged with an inner surface of the actuator lumen. The inner surface of the actuator lumen substantially constrains lateral movement of the tubular support and the flexible element.

23 Claims, 12 Drawing Sheets

U.S. PATENT DOCUMENTS

| | | |
|---|---|---|
| 7,588,555 B2 | 9/2009 | Pudelko et al. |
| 2003/0050598 A1* | 3/2003 | Hayzelden ............... 604/95.04 |
| 2005/0065467 A1 | 3/2005 | Pudelko et al. |

FOREIGN PATENT DOCUMENTS

| | | |
|---|---|---|
| EP | 1205208 A1 | 5/2002 |
| WO | WO-2005/030312 A1 | 4/2005 |

OTHER PUBLICATIONS

"U.S. Appl. No. 10/670,150, Response filed Dec. 10, 2008 to Non Final Office Action mailed Sep. 17, 2008", 13 pgs.

"U.S. Appl. No. 10/670,150, Advisory Action mailed May 13, 2008", 3 pgs.

"U.S. Appl. No. 10/670,150, Amendment and Response filed Jan. 31, 2007 to Non-Final Office Action mailed Nov. 1, 2006", 12 pgs.

"U.S. Appl. No. 10/670,150, Examiner Interview Summary filed Jun. 2, 2009", 1 pg.

"U.S. Appl. No. 10/670,150, Interview Summary mailed Feb. 5, 2007", 3 pgs.

"U.S. Appl. No. 10/670,150, Non-Final Office Action mailed Apr. 17, 2007", 4 pgs.

"U.S. Appl. No. 10/670,150, Non-Final Office Action mailed May 19, 2006", 5 pgs.

"U.S. Appl. No. 10/670,150, Non-Final Office Action mailed Sep. 17, 2008", 5 pgs.

"U.S. Appl. No. 10/670,150, Non-Final Office Action mailed Nov. 1, 2006", 5 pgs.

"U.S. Appl. No. 10/670,150, Notice of Allowance mailed May 5, 2009", 6 pgs.

"U.S. Appl. No. 10/670,150, Response filed Jun. 2, 2008 to Final Office Action mailed Dec. 31, 2007", 14 pgs.

"U.S. Appl. No. 10/670,150, Response filed Aug. 21, 2006 to Non-Final Office Action mailed May 19, 2006", 12 pgs.

"U.S. Appl. No. 10/670,150, Supplemental Notice of Allowability mailed Jun. 11, 2009", 4 pgs.

"U.S. Appl. No. 10/670,150, Amendment and Response filed Mar. 28, 2008 to Final Office Action mailed Dec. 31, 2007", 13 pgs.

"Canadian Application Serial No. 2,554,549, Office Action mailed Oct. 15, 2007", 2 pgs.

"Canadian Application Serial No. 2,554,549, Response filed Apr. 3, 2008 to Office Action mailed Oct. 15, 2007", 4 pgs.

"Canadian Application Serial No. 2554549, Office Action mailed Aug. 11, 2008", 2 pgs.

"Canadian Application Serial No. 2554549, Response filed Feb. 5, 2009 to Office Action mailed Aug. 11, 2008", 7 pgs.

"International Application Serial No. PCT/US2004/031431, International Preliminary Report on Patentability mailed Apr. 6, 2006", 10 pgs.

"International Application Serial No. PCT/US2004/031431, International Search Report mailed Feb. 21, 2005", 4 pgs.

"International Application Serial No. PCT/US2004/031431, Written Opinion mailed Feb. 21, 2005", 8 pgs.

* cited by examiner

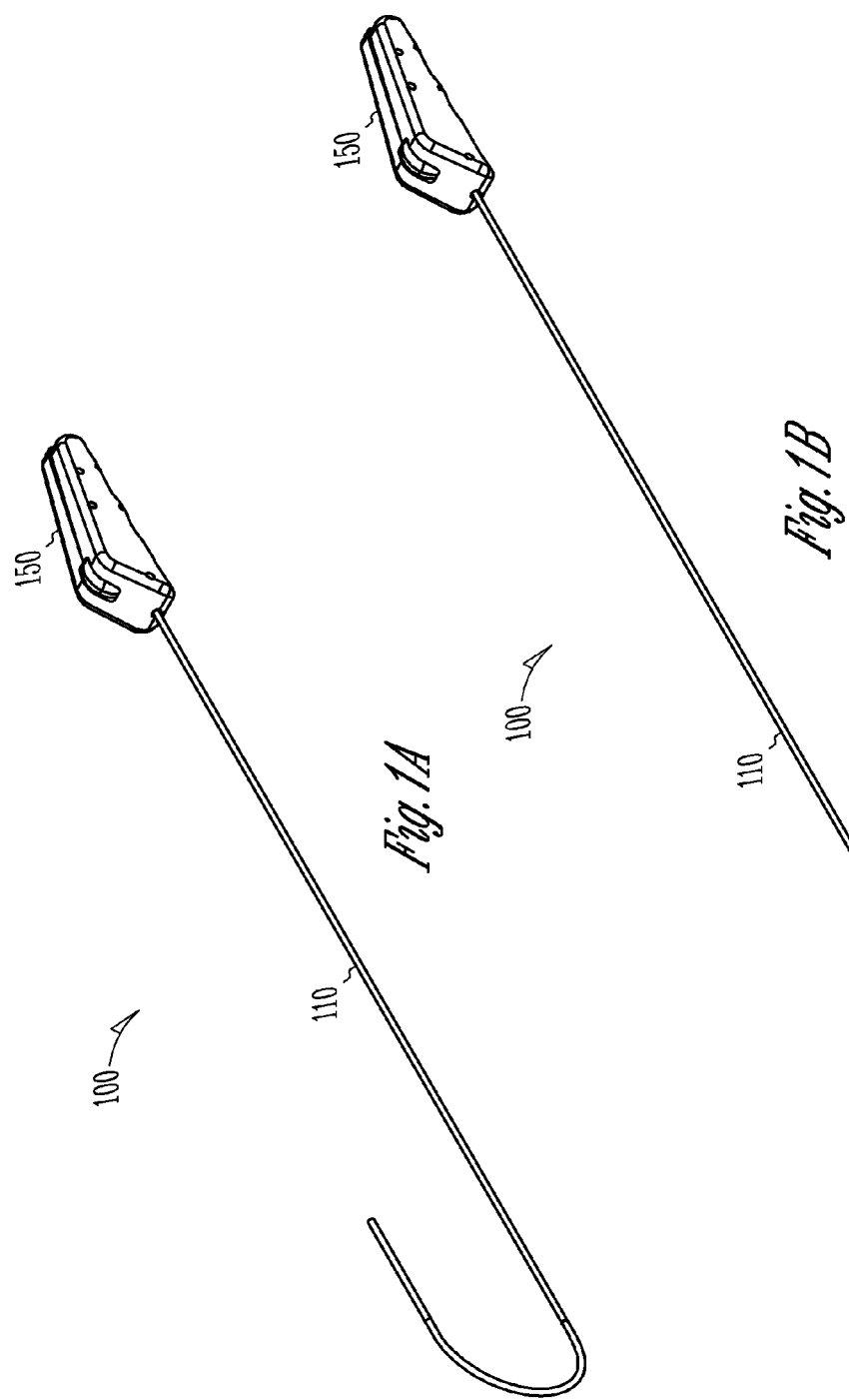

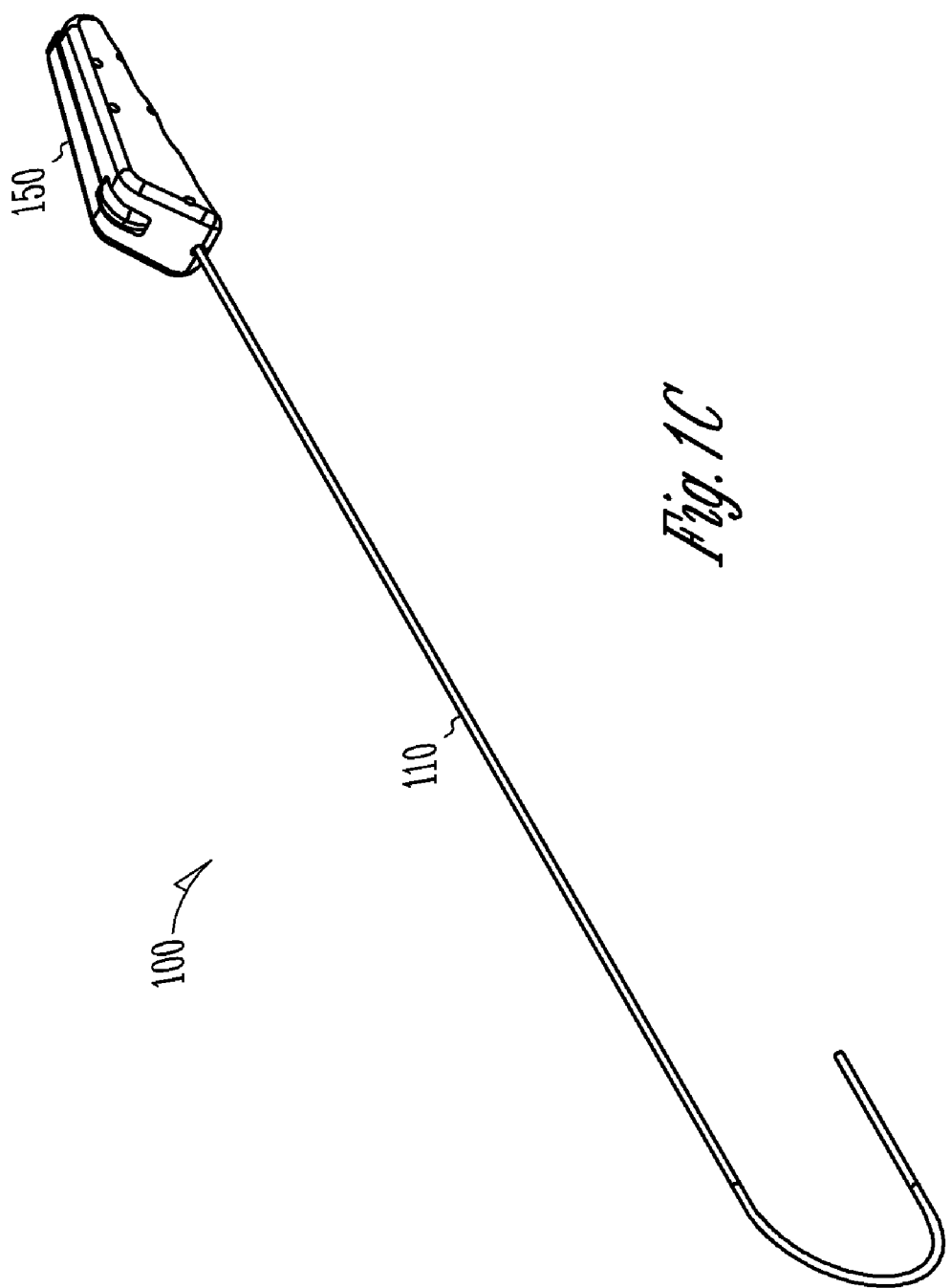

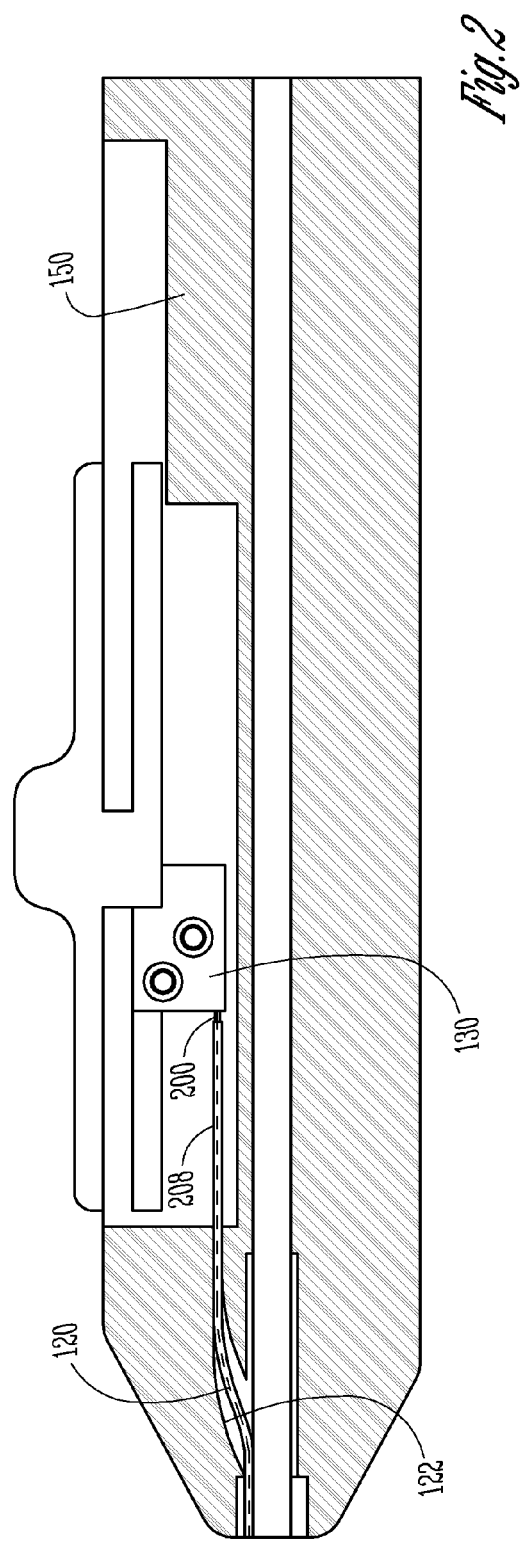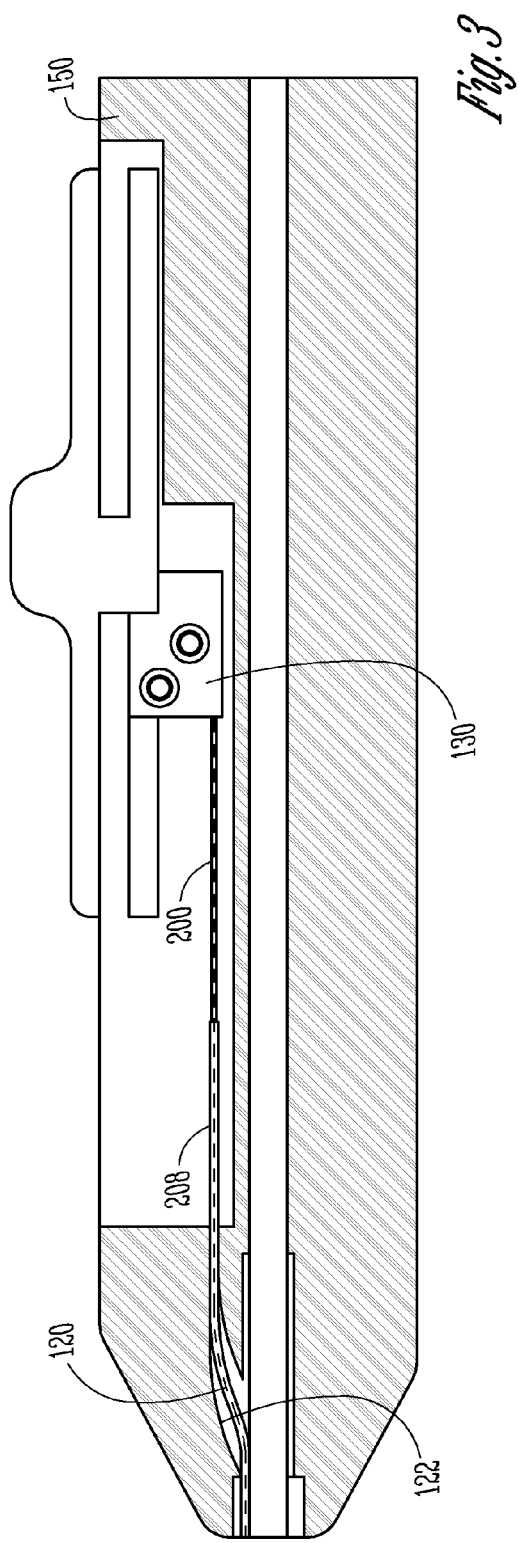

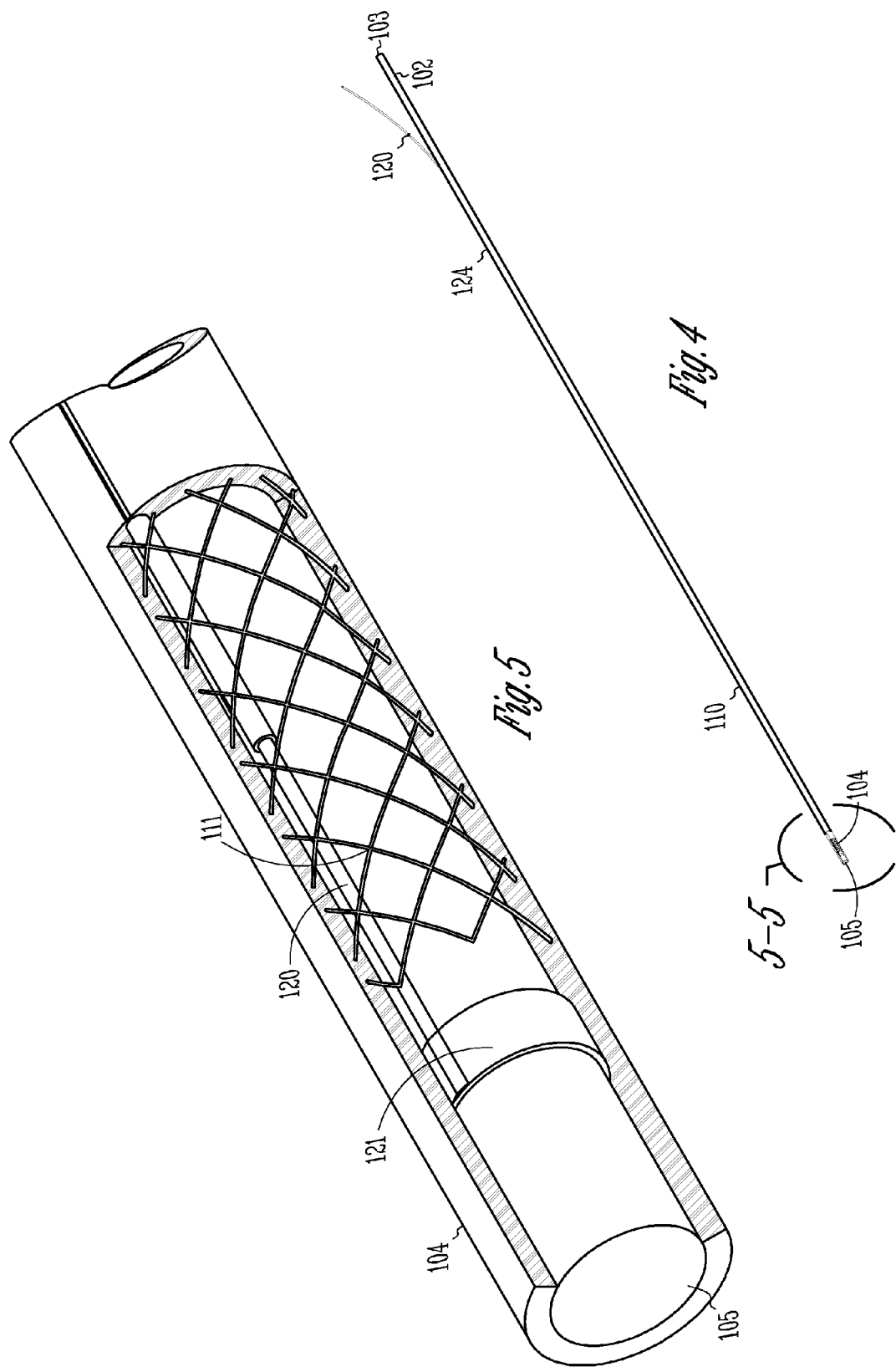

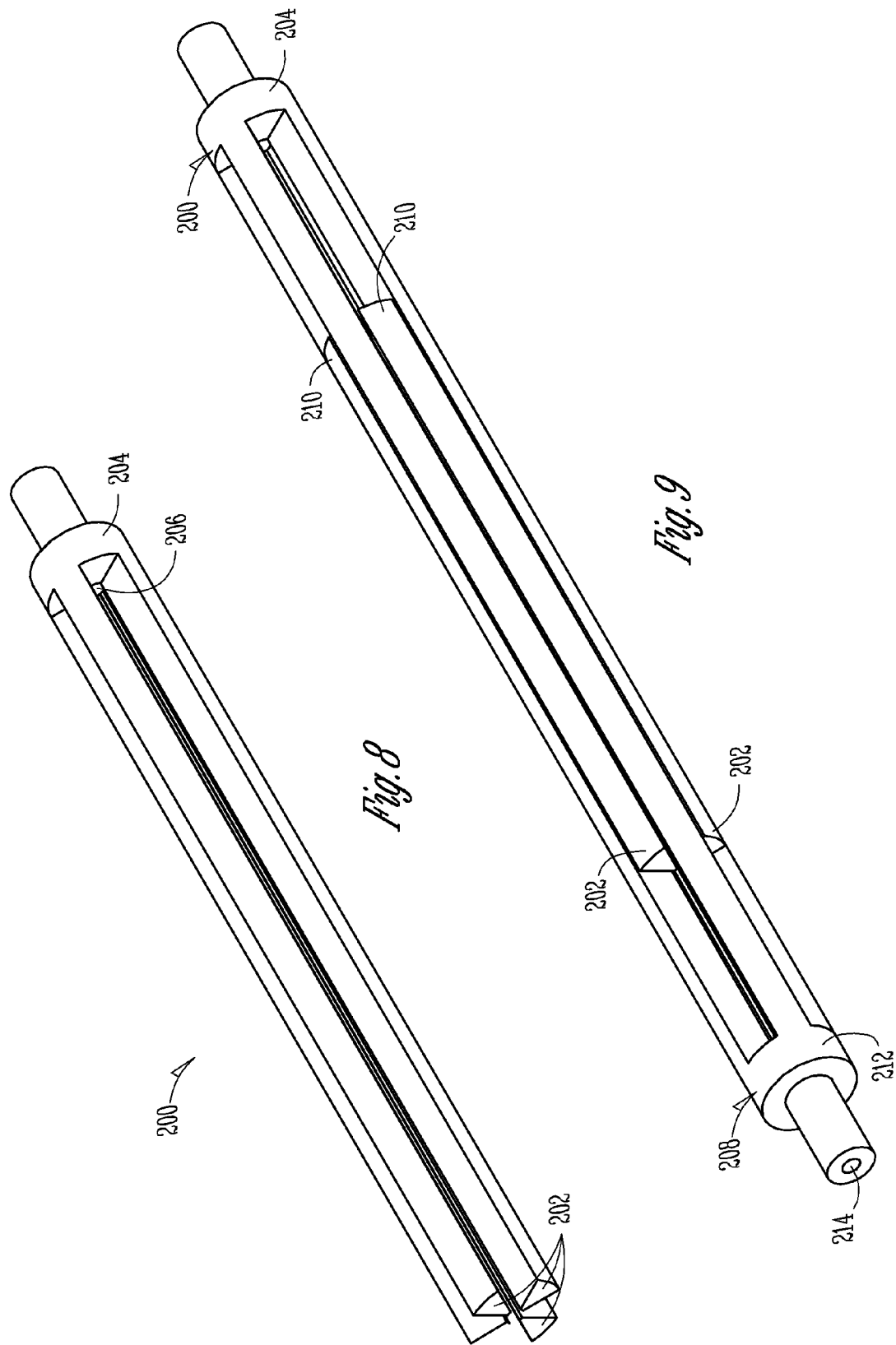

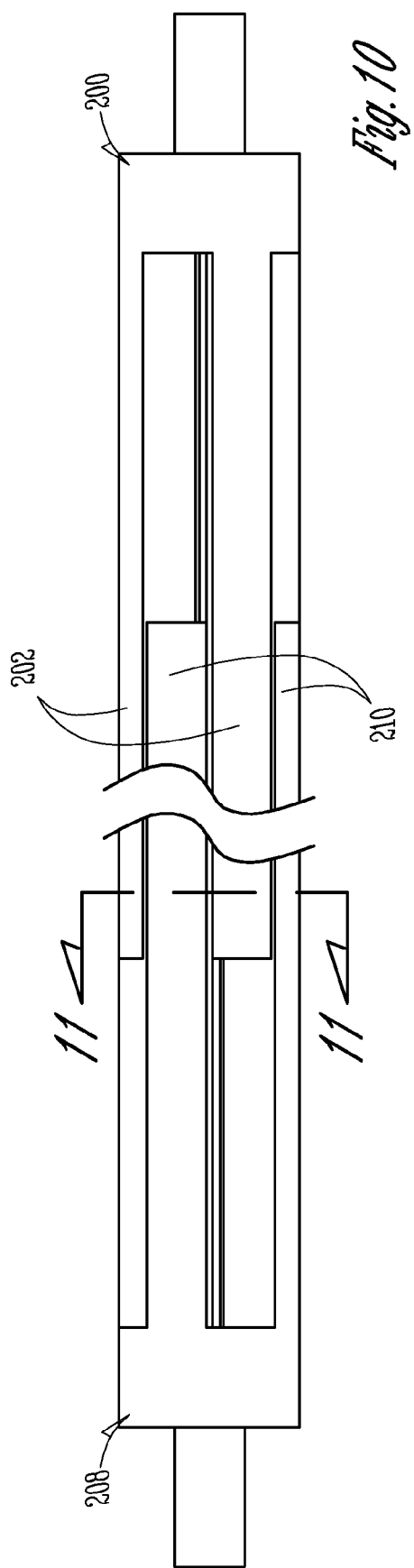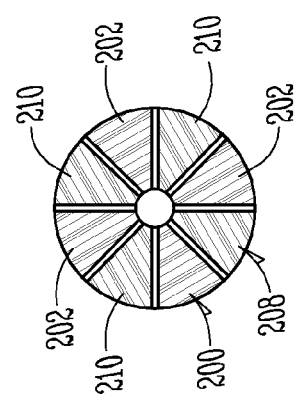

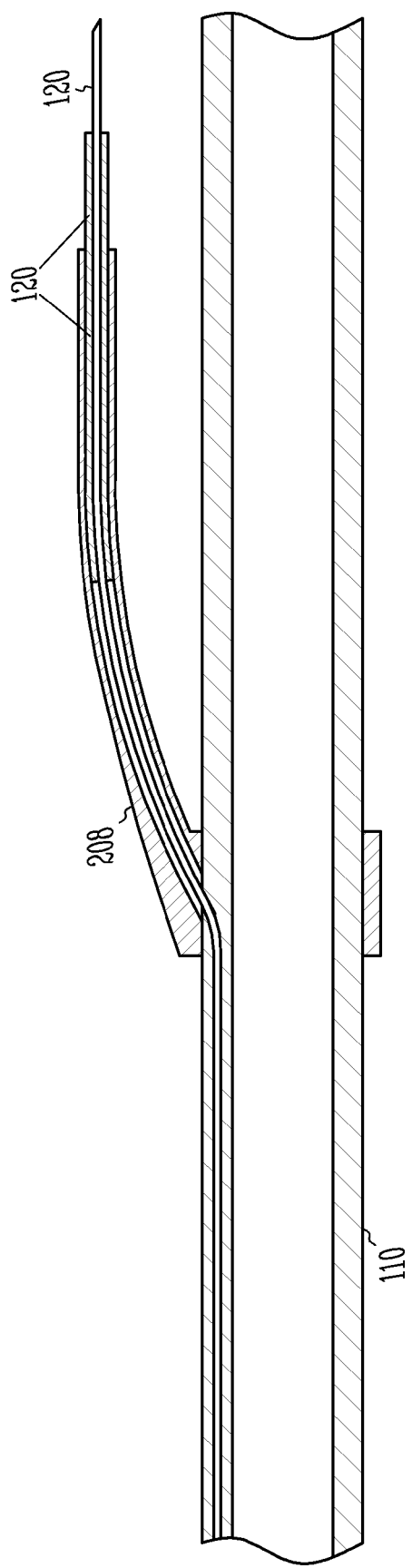

BI-DIRECTIONAL CATHETER ASSEMBLY AND METHOD THEREFOR

CROSS-REFERENCE TO RELATED APPLICATIONS

This application is a continuation of U.S. application Ser. No. 10/670,150, filed on Sep. 24, 2003, now U.S. Pat. No. 7,588,555, which is incorporated herein by reference.

TECHNICAL FIELD

The present invention relates generally to a deflectable catheter assembly. More particularly, it pertains to a bi-directional catheter assembly for a deflectable catheter assembly.

BACKGROUND

Increase in the use of stents, leads, and ablation techniques in branch vessels has provided an increased demand on the placement techniques for these devices. For some procedures, it is necessary to initially position a guidewire into a desired part of the lumen of a desired vessel or duct, such as a blood vessel. After the guidewire is positioned within the desired location, a catheter or other tubular device may be positioned over the guidewire and used to convey other medical instruments into the desired blood vessel or duct.

Alternatively, a guiding catheter is used to negotiate the vasculature of a patient. One example of a guiding catheter is described in U.S. Pat. No. 4,898,577 to Badger et al. The Badger guiding catheter includes a single elongate shaft that has a deflectable distal portion controllable by a pull wire. For bi-directional catheters, multiple pull wires are used to pull on the distal end and cause it to defect in more than one direction. One example of such a catheter is shown in U.S. Pat. No. 6,171,277. While bi-directional catheters are helpful, for example, in traversing a complex vasculature, conventional catheters are bulky and have a relatively large outer diameter given the use of multiple pull wires, or the size of the pull wires.

Accordingly, what is needed is a deflectable catheter that overcomes the shortcomings of previous bi-directional catheters. What is further needed is a catheter that allows for more accurate positioning of the distal end of the deflectable catheter, in a less traumatic way.

SUMMARY

A deflectable catheter assembly includes a catheter body and a housing coupled to a proximal end of the catheter body. A flexible element extends through the housing and an actuator lumen within the catheter body to a deflectable distal end. The deflectable distal end is controllable by the flexible element. A support assembly including a first tubular support is coupled to the flexible element and coupled to an actuator mechanism disposed within the housing.

Several options for the deflectable catheter assembly follow. For example, in one option, a second tubular support is telescopically coupled with the first tubular support and coupled to a surface defining the actuator lumen. In another option, an inner surface of the second tubular support is dimensioned and configured to snugly envelop and slidably couple with the flexible element. In yet another option, the outer surface of the first tubular support has a complementary perimeter dimensioned and configured to slidably couple with the surface defining the actuator lumen. The surface defining the actuator lumen has a circular geometry, in one option. In still another option, a first tubular support intermediate surface and second tubular support intermediate surface slidably couple the first tubular support with the second tubular support.

In another embodiment, a method comprises manipulating a deflectable catheter assembly into a first orientation, the catheter assembly includes a catheter body and a housing coupled to a proximal end of the catheter body. An actuator lumen extends through the catheter body, and a flexible element extends from an actuator member coupled with the housing to a deflectable distal end. A first tubular support is coupled to the flexible element and coupled to the actuator member. A second tubular member is coupled to a surface defining the actuator lumen and coupled to the flexible element. The method further includes constraining lateral movement of the flexible element, including bracing the flexible element with the first tubular support and second tubular support. Additionally, the method includes further manipulating the actuator member to actuate the flexible element and thereby deflect the deflectable distal end into a disparate orientation.

Several options for the method follow. In one option, the first tubular support and actuator member are telescopically advanced with respect to the second tubular support. In another option, further manipulating the actuator member to deflect the deflectable distal end into a disparate orientation includes constraining lateral movement of the flexible element within the actuator lumen with the first tubular support and second tubular support.

In yet another embodiment, a method comprises manipulating a deflectable catheter assembly into a first orientation, the catheter assembly includes a catheter body and housing coupled to the proximal end of the catheter body. An actuator lumen extends through the catheter body, and a flexible element extends within the actuator lumen. The flexible element extends from an actuator member coupled with the housing to a deflectable distal end. A first tubular support is coupled to the flexible element and coupled to the actuator member. A second tubular support is coupled to a surface defining the actuator lumen and slidably coupled to the flexible element. The method further includes, longitudinally advancing the flexible element and first tubular support along the longitudinal axis of the actuator lumen. The second tubular support is stationary with respect to the housing. The first tubular support and second tubular support remain aligned with the actuator lumen longitudinal axis. Additionally, the method includes further manipulating the actuator member to advance the flexible element and deflect the deflectable distal end into a disparate orientation.

Several options for the method follow. In one option, the first tubular support and actuator member are telescopically advanced with respect to the second tubular support. In another option, the method further includes constraining lateral movement of the flexible element including bracing the flexible element with the first tubular support and second tubular support. In yet another option, further manipulating the actuator member to deflect the deflectable distal end into a disparate orientation includes constraining lateral movement of the flexible element within the actuator lumen with the first tubular support and second tubular support. Additionally, another option for further manipulating the actuator member includes longitudinally advancing the flexible element and first tubular support along the longitudinal axis of the actuator lumen, while the second tubular support is stationary with respect to the housing, and the first tubular support and second tubular support remain aligned with the actuator lumen longitudinal axis.

The deflectable catheter allows for bi-directional deflection of the catheter body using a single pull wire having a smaller diameter than what is otherwise required. The tubular supports brace the narrow pull wire when compressed to prevent buckling due to articulation of the catheter into a disparate orientation from that caused by tensioning. Consequently, the pull wire and support assembly require significantly less volume within the catheter and leave additional space for the delivery lumen while allowing bi-directional deflection of the catheter.

Furthermore, the telescopic movement of one support member with respect to another allows bracing of the pull wire under any deflection of the catheter caused by compression. Consequently, any desired bi-directional deflection of the catheter is available where the support assembly is used with the narrow pull wire.

These and other embodiments, aspects, advantages, and features of the present invention will be set forth in part in the description which follows, and in part will become apparent to those skilled in the art by reference to the following description of the invention and referenced drawings or by practice of the invention. The aspects, advantages, and features of the invention are realized and attained by means of the instrumentalities, procedures, and combinations particularly pointed out in the appended claims and their equivalents.

BRIEF DESCRIPTION OF THE DRAWINGS

FIG. 1A is a perspective view illustrating a deflectable catheter assembly constructed in accordance with one embodiment.

FIG. 1B is a perspective view illustrating a deflectable catheter assembly constructed in accordance with one embodiment.

FIG. 1C is a perspective view illustrating a deflectable catheter assembly constructed in accordance with one embodiment.

FIG. 2 is a cross-sectional view illustrating a portion of the deflectable catheter assembly constructed in accordance with one embodiment.

FIG. 3 is a cross-sectional view illustrating a portion of the deflectable catheter assembly constructed in accordance with one embodiment.

FIG. 4 is a perspective view illustrating a deflectable catheter body constructed in accordance with one embodiment.

FIG. 5 is a perspective view illustrating a distal portion of the deflectable catheter body constructed in accordance with one embodiment.

FIG. 8 is a perspective view illustrating a tubular support member constructed in accordance with one embodiment.

FIG. 9 is a perspective view illustrating tubular support members telescopically engaged in accordance with one embodiment.

FIG. 10 is a side view illustrating tubular support members shown in FIG. 9.

FIG. 11 is a cross-sectional view illustrating the tubular support members shown along line 11-11 in FIG. 10.

FIG. 18 is a cross-sectional view illustrating tubular support members telescopically engaged in accordance with one embodiment.

DESCRIPTION OF THE EMBODIMENTS

Figure 6:
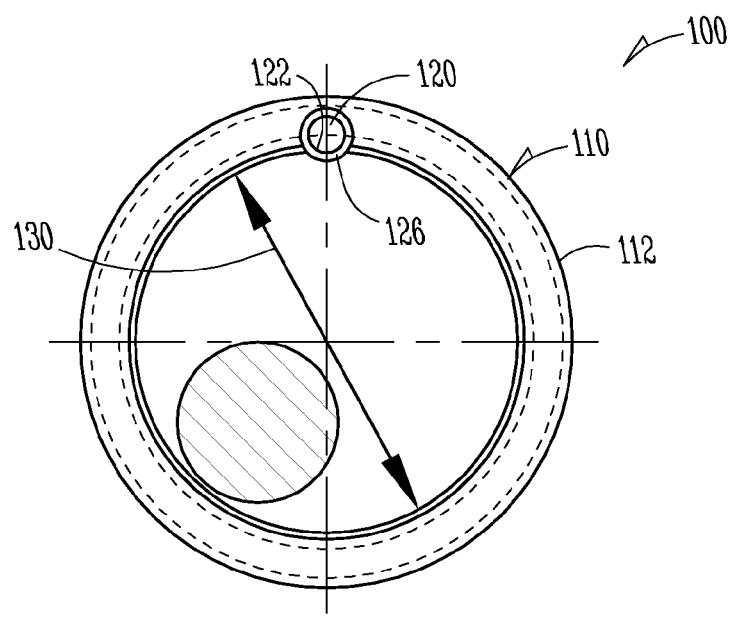
FIG. 6 is an end view of the distal end of the deflectable catheter assembly constructed in accordance with one embodiment.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural changes may be made without departing from the scope of the present invention. Therefore, the following detailed description is not to be taken in a limiting sense, and the scope of the subject matter of this application is defined by the appended claims and their equivalents.

FIGS. 1A, 1B and 1C illustrate a deflectable catheter assembly 100, where FIG. 1A illustrates the deflectable catheter assembly 100 in one articulated position, and FIG. 1C illustrates the catheter assembly 100 in another articulated orientation. FIG. 1B illustrates the deflectable catheter assembly 100 in an unarticulated position. The deflectable catheter assembly 100 includes a catheter body 110 and a handle assembly 150 that houses steering mechanisms for deflection of the catheter body 110. The handle assembly 150 allows for the selectable deflection of a distal end of the catheter body 110 into any number of disparate orientations. One example of the handle assembly 150 is described in co-pending application Ser. No. 10/179,633, assigned to MedAmicus, Inc., and is entitled "Articulating Handle For a Deflectable Catheter," which is incorporated herein by reference. FIGS. 2 and 3 illustrate one option where a flexible element, such as a pull wire 120, is connected to an actuator mechanism 130 that is slid or rotated to apply tension or compression to the pull wire 120. As shown in FIGS. 1A and 1C, when tension or compression is applied to the pull wire 120, the pull wire anchor (described below) at the distal end of the catheter body 110 is pulled or pushed causing the distal portion of the catheter body 110 to curve in predetermined directions.

With reference to FIG. 4, the catheter body 110 comprises an elongate tubular construction that is flexible yet substantially non-compressible along its length. The deflectable catheter body 110 extends from a proximal end 102 to a deflectable distal end 104, where the deflectable distal end 104 is adapted to be disposed within a patient. At the proximal end 102 is a proximal tip 103, and at the distal end 104 is a distal tip 105. At the proximal end 102, the physician controls the deflection of the deflectable catheter body 110 with the handle assembly 150 (FIGS. 1A, 1B, 1C, 2 and 3) containing the actuator mechanism 130 (FIGS. 2 and 3) and a pull wire 120 (FIGS. 2 and 3), as further described below. The distal end 104 is deflected to traverse various branch vessels with the catheter assembly 100 (FIGS. 1A and 1C).

FIG. 5 illustrates a partial cut-away view of FIG. 4, including the distal end 104 of the catheter body 110. The catheter body 110 includes a pull wire anchor 121 that is secured to the catheter body 110. The pull wire 120 is secured to the pull wire anchor 121. It should be noted that the pull wire 120 can be secured to the distal end 104 of the catheter body 110 by other means. In one option, the catheter body 110 includes a stiffening member embedded therein, such as a braided stainless steel member 111. The stiffening member facilitates rotation of the distal end 104 from the proximal end 102, and also assists in preventing the catheter body 110 from collapsing.

Figure 7:
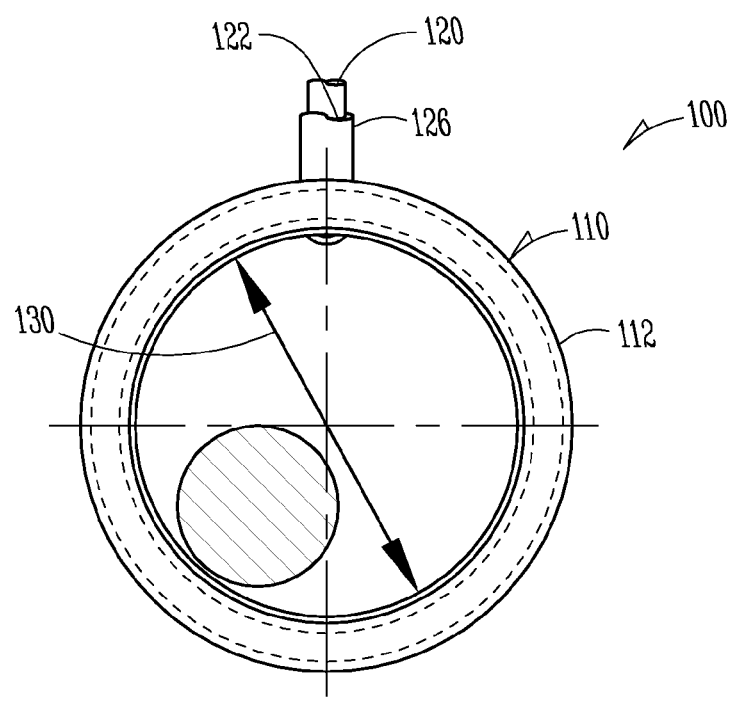
FIG. 7 is a front view of the proximal end of the deflectable catheter assembly constructed in accordance with one embodiment.

As shown in FIGS. 6 and 7 the pull wire 120 is received within an actuator lumen 122. The actuator lumen 122 is disposed within the catheter body 110 and handle assembly 150 (see FIGS. 2 and 3). The pull wire 120 is movably disposed within the actuator lumen 122. In one example, the actuator lumen 122 extends from a location near or at the distal end 104 (see FIG. 5) to an intermediate location that does not extend through the proximal end 102 (see FIG. 4). For example, as shown in FIG. 4, when the pull wire 120 exits the catheter body 110 near the proximal end 102 the actuator lumen 122 consequently exits at a location in a side wall 124 of the catheter body 110. FIG. 7 illustrates an end view of the catheter body 110 at the proximal end 102. The lumen 122 does not extend to the proximal end 102 nor to the proximal tip 103 of the catheter body 110. Therefore, there is no cross-contamination of fluids or gasses from a delivery lumen to the actuator lumen 122, or vice versa. As shown in FIGS. 2 and 3, in another example, the actuator lumen 122 extends through the proximal end 102 (see FIG. 4) and into the handle assembly 150 (see FIGS. 2 and 3).

Figure 16:
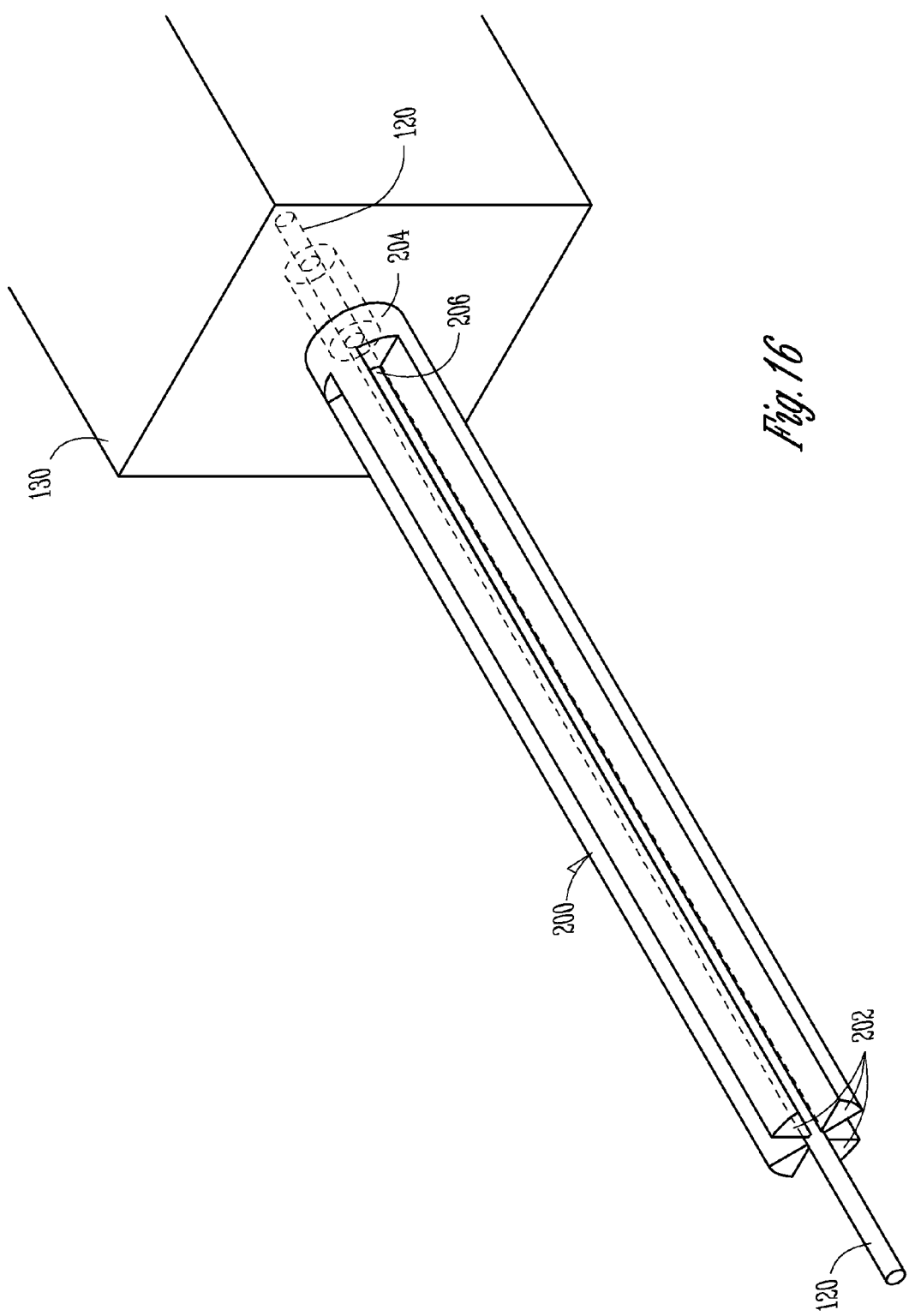
FIG. 16 is a perspective view illustrating a tubular support member engaged in accordance with one embodiment.

The following is one example of how to construct the pull wire support assembly. It should be noted that several variations exist, including, for example, interposed telescoping members. With reference to FIG. 8, in one option a first tubular support member 200 is shown that is aligned along the longitudinal axis of the actuator lumen 122. The first tubular support member 200 presents one or more fingers 202 that extend from a base 204 parallel to a longitudinal axis of the member 200. As shown in FIG. 16, in one option, the first tubular support member 200 is coupled with the pull wire 120 and fixedly coupled with the actuator mechanism 130. In another option, the first tubular support member 200 is fixedly coupled to the pull wire 120. In yet another option, the first tubular support member 200 is fixedly coupled to both the pull wire 120 and actuator mechanism 130. In one example, the first tubular support member 200 extends from a proximal end adjacent the actuator mechanism 130 to a distal end within actuator lumen 122. The distal end of the first tubular support member 200 is selectively positioned (described below) between the actuator mechanism 130 and the exit point (described above) of the pull wire 120 from catheter body 110.

Figure 12:
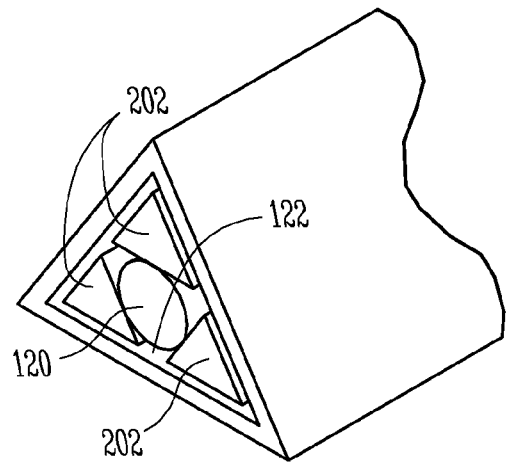
FIG. 12 is a front view illustrating a tubular support member telescopically engaged in accordance with one embodiment.
Figure 13:
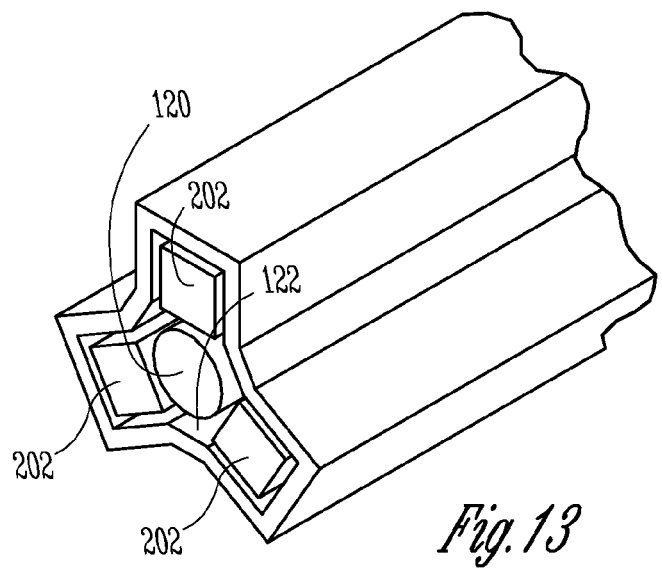
FIG. 13 is a front view illustrating a tubular support member telescopically engaged in accordance with one embodiment.
Figure 14:
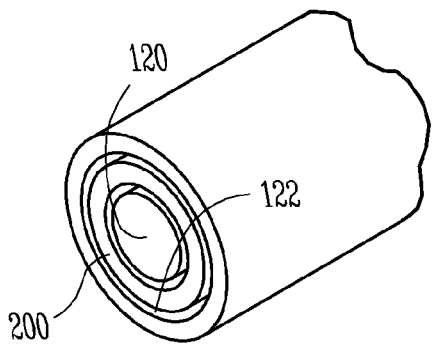
FIG. 14 is a front view illustrating a tubular support member telescopically engaged in accordance with one embodiment.

Several means exist for snugly coupling the first tubular support member 200 with the surface defining the actuator lumen 122. In the following options the outer surfaces of the fingers 202 and base 204 define a perimeter dimensioned and configured to enable the first tubular support member 200 to be housed within the actuator lumen 122. In one option, the outer surfaces of the fingers 202 and base 204 are dimensioned and configured to be coupled within an actuator lumen 122 having a circular cross-section. The fingers 202 and base 204 have a substantially circular outer geometry so as to complement the circular actuator lumen 122. In another option, shown in FIG. 12, the actuator lumen 122 has a triangular cross-section geometry. The outer surfaces of the fingers 202 and base 204 have a complementary triangular geometry so as to be snugly coupled within the triangular actuator lumen 122. In yet another option, shown in FIG. 13, the actuator lumen 122 has a cross-section geometry resembling an inverted 'Y' or three pointed star. Each 'point' of the actuator lumen 122 has a square furrow. The outer surfaces of the fingers 202 and base 204 have a complementary square geometry so as to be snugly coupled within the actuator lumen 122. In still another option, shown in FIG. 14, the first tubular support member 200 is a cylindrical member without fingers.

Figure 17:
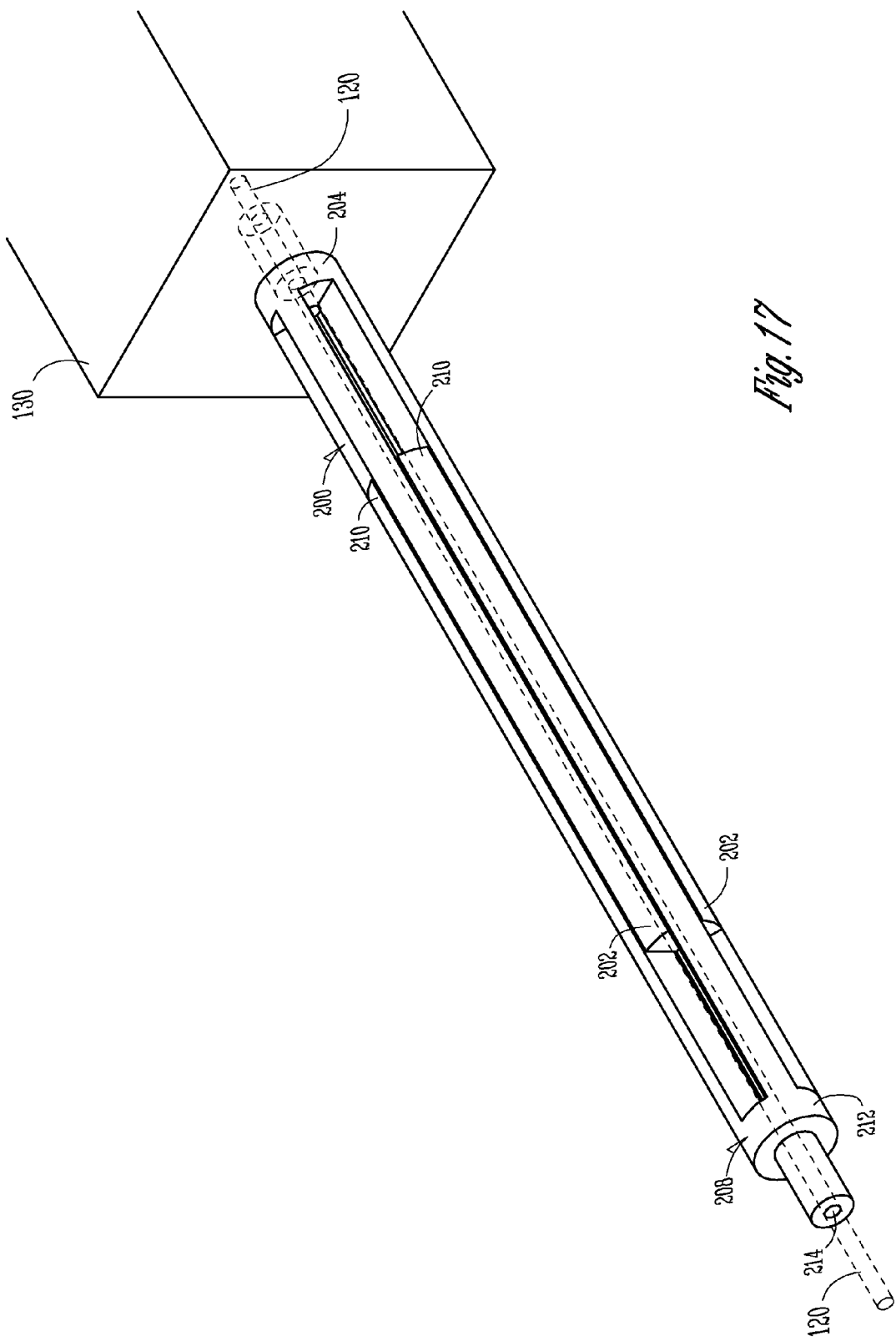
FIG. 17 is a perspective view illustrating tubular support members telescopically engaged in accordance with one embodiment.

Referring again to FIG. 8, where the first tubular support member 200 presents fingers 202, a pull wire lumen 206 is provided about the longitudinal axis of the first tubular support member 200 and extends through the base 204. The inner surfaces of the fingers 202 further define the pull wire lumen 206. As shown in FIGS. 16 and 17, in one option, the pull wire 120 is coupled to the inner surfaces of the fingers 202 and the base 204 within the pull wire lumen 206. The first tubular support member 200 is dimensioned and configured to restrain the pull wire 120 from moving laterally with respect to the longitudinal axis of the first tubular support member 200. In one example, the diameter of the pull wire 120 is only substantially similar or slightly smaller than the diameter of the pull wire lumen 206, and thus the first tubular support member 200 prevents lateral movement of the pull wire 120.

As shown in FIGS. 9 and 10, in one example, the first tubular support member 200 is telescopically coupled with a second tubular support member 208. The second tubular support member 208 has a complementary geometry to that of the first tubular support member 200. For example, the second tubular support member 208 presents fingers 210 that extend from a base 212 parallel to a longitudinal axis of the member 208. FIG. 11 shows fingers 202, 210 dimensioned and configured to slidably couple with each other and thereby allow telescoping movement between the first tubular support member 200 and the second tubular support member 208. In this example, the fingers 210 and base 212 of the second tubular support member 208 are dimensioned and configured to fit within the perimeter defined by the outer surfaces of the fingers 202 and base 204 of the first tubular support member 200 (described above). In one option, the second tubular support member 208 is coupled to the housing 150, disposed within the actuator lumen 122, and aligned along the longitudinal axis of the actuator lumen 122. As shown in FIG. 2, the proximal end of the second tubular support member 208 is disposed within actuator lumen 122 adjacent to the location actuator mechanism 130 assumes when pull wire 120 is fully compressed. The second tubular support member 208 extends from the proximal end to a distal end disposed where the actuator lumen 122 exits the catheter body 110 (described above). In one option, the first tubular support member 200 and second tubular support member 208 have a substantially similar outer perimeter. In another option, the first tubular support member 200 and second tubular support member 208 are dimensioned and configured to snugly couple with the surface defining the actuator lumen 122. The first tubular support member 200 and second tubular support member 208 are constructed from stainless steel, but may also be fabricated from other durable metals or plastics, including flexible materials.

Figure 15:
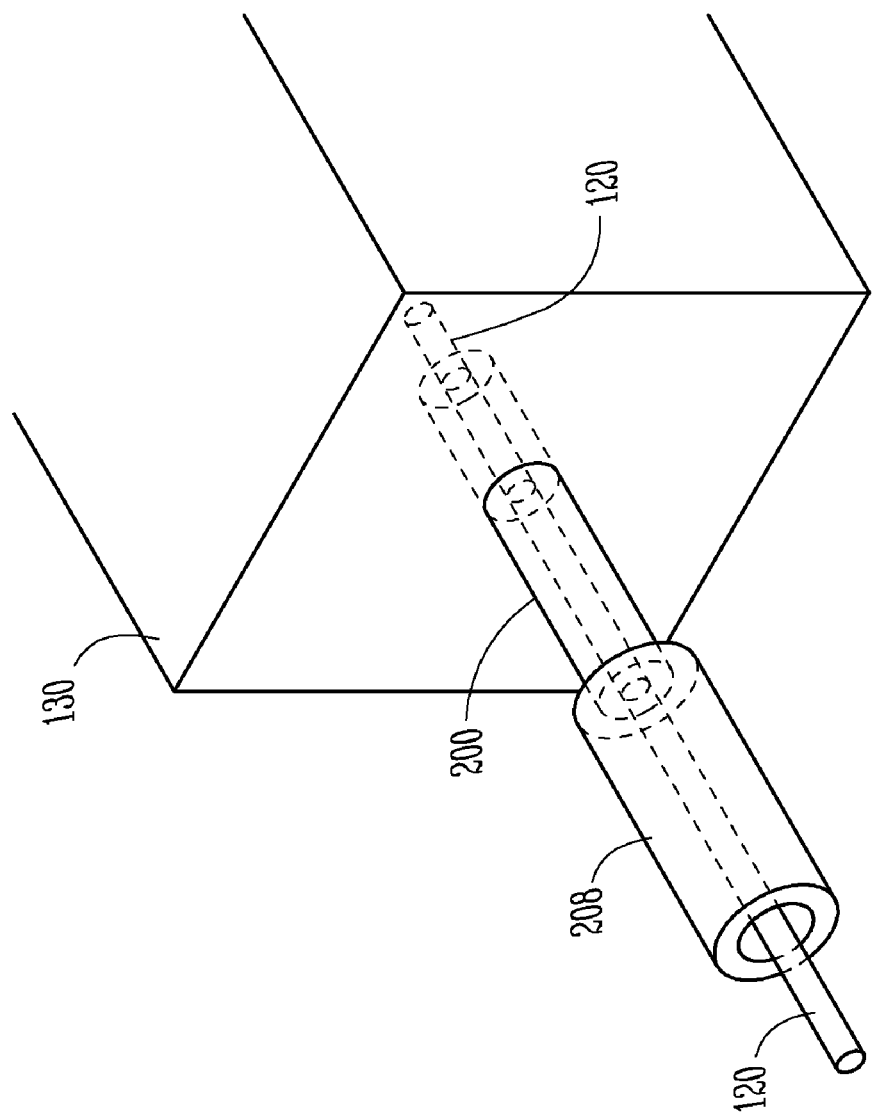
FIG. 15 is a perspective view illustrating tubular support members telescopically engaged in accordance with one embodiment.

Referring again to FIG. 9, a pull wire lumen 214 is provided in the second tubular support member 208. The pull wire lumen 214 is provided about the longitudinal axis of the second tubular support member 208, extends through the base 212 and is further defined by the inner surfaces of the fingers 210. As shown in FIG. 17, in one option, the pull wire 120 is received within the pull wire lumen 214 and is slidably coupled to the second tubular support member 208 therein. In one option, the pull wire 120 is slidably coupled to the inner surfaces of the fingers 210 and the base 212. The second tubular support member 208, in one option, is dimensioned and configured to restrain the pull wire 120 from moving laterally with respect to the longitudinal axis of the second tubular support member 208. As shown in FIG. 15, in another option, the second tubular support member 208 is a cylindrical member without fingers which has a complementary inner surface geometry to the outer surface of the first tubular support member 200, and is therefore slidably coupled with the first tubular support member 200 to allow slidable movement therebetween.

In still another option, as shown in FIG. 18, the second tubular support 208 is formed on the catheter body 110. In other words, the second tubular support member 208 is coupled to the catheter body 110 and extends from a distal end where pull wire 120 exits the catheter body to a proximal end. In one option, the second tubular support member 208 comprises at least a portion of the surface defining the actuator lumen 122. In another option, the outer surface of the second tubular support member 208 is coupled to the surface defining the actuator lumen 122. Optionally, the second tubular support member 208 is plastic and overmolded onto the catheter body 110. The second tubular support member 208 has a complementary inner surface geometry to the outer surface of the first tubular support member 200. The first tubular 200 is therefore slidably coupled with the second tubular support member 208 to allow slidable movement therebetween. In one example, the pull wire 120 is encapsulated with a sleeve including braided stainless steel impregnated with PTFE. In one option, the sleeve surrounds the first tubular member 200, but is not bonded to the first tubular support member or the pull wire 120. The second tubular support member 208 bonds with the sleeve when overmolded onto the catheter body 110. The sleeve prevents bonding of the second tubular support member 208 to the pull wire 120 and allows slidable movement between the first tubular support member 200 and second tubular support member.

In operation in one example, the first tubular support member 200 and second tubular support member 208 proximately abut the pull wire 120, but do not otherwise interfere with longitudinal movement of the pull wire 120. As best shown in FIG. 17, when the actuator 130 applies tension or compression to the pull wire 120 so as to deflect the catheter body 110, the first tubular support member 200 advances telescopically with respect to the second tubular support member 208 and actuator lumen 122 as it is fixedly coupled to the actuator mechanism 130. When the pull wire 120 is specifically compressed, which occurs when it is desired that the catheter body 110 be oriented oppositely from an orientation caused with tension, this abutment by the tubular support members 200, 208 braces the pull wire 120 and prevents it from buckling. Further, the telescoping movement of the first tubular support member 200 with respect to the second tubular support member 208 ensures that the compressed pull wire 120 is braced against buckling while the catheter body 110 is deflected to any degree.

As illustrated in FIG. 15, in another example, the cylindrical second tubular support member 208 slidably couples with, but does not interfere with the movement of the cylindrical first tubular support member 200 (as described above). In one option, the first tubular support member 200 is coupled to the pull wire 120 and fixedly coupled to the actuator mechanism 130, but does not interfere with longitudinal movement of the pull wire 120. When the actuator 130 applies tension or compression to the pull wire 120 so as to deflect the catheter body 110, the first tubular support member 200 moves telescopically with respect to the second tubular support member 208 as it is fixedly coupled to the actuator mechanism 130. When the pull wire 120 is specifically compressed, which occurs when it is desired that the catheter body 110 be oriented oppositely from an orientation caused with tension, the abutment by the first tubular support member 200 and the slidable coupling between the first tubular support member 200 and second tubular support member 208 braces the pull wire 120 and prevents it from buckling.

In yet another example, a first tubular support member 200 having a triangular or inverted 'Y' geometry within a complementary actuator lumen 122 is coupled to the pull wire 120 and is fixedly coupled to the actuator mechanism 130, but does not interfere with longitudinal movement of the pull wire 120. When the actuator 130 applies tension or compression to the pull wire 120 so as to deflect the catheter body 110, the first tubular support member 200 slidably moves within the actuator lumen 122 as it is fixedly coupled to the actuator mechanism 130. When the pull wire 120 is specifically compressed, which occurs when it is desired that the catheter body 110 be oriented oppositely from an orientation caused with tension, the first tubular support member 200 braces the pull wire 120 and prevents it from buckling.

In another embodiment, a method comprises manipulating a deflectable catheter assembly into a first orientation, the deflectable catheter assembly including a catheter body and housing attached to the catheter body, an actuator lumen extends therein. The housing is attached to the catheter body proximal end, and a flexible element extends from an actuator member within the housing through the actuator lumen to a deflectable distal end. A first tubular support member is coupled to the flexible element and fixedly coupled to the actuator member, and a second tubular support member is slidably coupled with the first tubular support member and slidably coupled to the flexible element. The first tubular support member and second tubular support member constrain lateral movement of the flexible element within the actuator lumen. In one option, the method includes longitudinally or telescopically advancing the flexible element and first tubular support member along the actuator lumen longitudinal axis. When the flexible element and first tubular support member are advanced, the second tubular support member is stationary with respect to the housing and the first tubular support member and second tubular support member remain aligned with the actuator lumen longitudinal axis. Additionally, the method includes further manipulating the actuator member to thereby actuate the flexible element and deflect the deflectable distal end into a disparate orientation. Furthermore, the method includes steering the deflectable catheter assembly which includes further manipulating the actuator member to deflect the deflectable distal end.

Several options for the method are as follows. For example, in one option, manipulating the actuator member to deflect the deflectable distal end into a disparate orientation includes constraining lateral movement of the flexible element within the actuator lumen with the first tubular support member and second tubular support member. In another option, further manipulating the actuator member to deflect the deflectable distal end into a disparate orientation includes longitudinally advancing the flexible element and first tubular support member along the actuator lumen longitudinal axis, while the second tubular support member is stationary with respect to the housing, and the first tubular support member and second tubular support member remain aligned with the actuator lumen longitudinal axis.

Advantageously, the above described deflectable catheter allows for bi-directional deflection of the catheter body using a single pull wire having a smaller diameter than what is otherwise required. The pull wire support assembly provides bracing for the narrow pull wire, when compressed, that prevents buckling due to articulation of the catheter into a disparate orientation from that caused by tensioning. Consequently, the pull wire and support assembly require significantly less volume within the catheter and leave additional space for the delivery lumen while allowing bi-directional deflection of the catheter.

Furthermore, the telescopic movement of one support member with respect to another allows bracing of the pull wire under any deflection of the catheter caused by compression. Consequently, any desired bi-directional deflection of the catheter is available where the support assembly is used with the narrow pull wire.

It is to be understood that the above description is intended to be illustrative, and not restrictive. Many other embodiments will be apparent to those of skill in the art upon reading and understanding the above description. It should be noted that embodiments discussed in different portions of the description or referred to in different drawings can be combined to form additional embodiments of the present invention. The scope of the invention should, therefore, be determined with reference to the appended claims, along with the full scope of equivalents to which such claims are entitled.

What is claimed is:

1. A deflectable catheter assembly comprising:
   a) a catheter body comprising a sidewall defined by spaced apart interior and exterior surfaces extending from a deflectable distal end to a proximal end;
   b) an actuator lumen positioned in the catheter sidewall between the interior and exterior surfaces of the catheter body;
   c) a housing engaged to the proximal end of the catheter body;
   d) a flexible element extending from the housing through the actuator lumen to the deflectable distal end, wherein the deflectable distal end is deflected by pushing and pulling of the flexible element;
   e) an actuator movably coupled with the housing and connected to the flexible element;
   f) a tubular support engaged around the flexible element and connected to the actuator, wherein the tubular support, which moves with the actuator, substantially constrains lateral movement of the flexible element; and
   g) the tubular support is telescopically received and engaged with an inner surface of the actuator lumen, which inner surface substantially constrains lateral movement of the tubular support and the flexible element.

2. The deflectable catheter assembly of claim 1 wherein at least a portion of the actuator lumen extends from near the proximal end to the deflectable distal end.

3. The deflectable catheter assembly of claim 1 wherein the tubular support snugly envelops the flexible element.

4. The deflectable catheter assembly of claim 1 wherein one or more of the inner surface of the actuator lumen or the tubular support continuously constrains the flexible element from lateral movement between the deflectable distal end and the actuator.

5. The deflectable catheter assembly of claim 1 wherein the flexible element extends out of the catheter body at an intermediate portion between the deflectable distal end and the proximal end.

6. The deflectable catheter assembly of claim 5 wherein the tubular support is slidably engaged with the inner surface of the actuator lumen adjacent the intermediate portion.

7. The deflectable catheter assembly of claim 1 wherein the inner surface of the actuator lumen is a second tubular support.

8. A deflectable catheter assembly comprising:
   a) a catheter body extending from a deflectable distal end to a proximal end, wherein the catheter body includes an actuator lumen extending from the deflectable distal end toward the proximal end;
   b) a housing engaged to the proximal end of the catheter body;
   c) a flexible element extending from the housing through the actuator lumen to the deflectable distal end, and adjacent the proximal end at least a flexible element first portion extends outside of the actuator lumen at an angle relative to a flexible element second portion within the actuator lumen;
   d) an actuator movable relative to the housing and connected to the flexible element, wherein the actuator is movable between a proximal actuator position and a distal actuator position;
   e) a flexible element bracing assembly including:
      i) a tubular support engaged around at least the flexible element first portion outside of the actuator lumen and telescopically received within the actuator lumen, wherein the tubular support maintains the flexible element first portion at the angle relative to the flexible element second portion,
      ii) an inner surface of the actuator lumen engaged around at least the flexible element second portion within the actuator lumen, and
      iii) the tubular support and the inner surface of the actuator lumen brace the flexible element from lateral movement throughout proximal and distal movement of the actuator and the flexible element from the proximal actuator position to the distal actuator position.

9. The deflectable catheter assembly of claim 8 wherein at least a portion of the actuator lumen is positioned inside a catheter body sidewall between a catheter body interior surface and a catheter body exterior surface.

10. The deflectable catheter assembly of claim 8 wherein the tubular support snugly envelops at least the flexible element first portion.

11. The deflectable catheter assembly of claim 8 wherein the inner surface of the actuator lumen snugly envelops and slidably engages with at least the flexible element second portion.

12. The deflectable catheter assembly of claim 8 wherein the flexible element extends out of the catheter body and the actuator lumen at an intermediate portion of the catheter body between the deflectable distal end and the proximal end.

13. The deflectable catheter assembly of claim 12 wherein the tubular support is telescopically received within the actuator lumen adjacent the intermediate portion.

14. The deflectable catheter assembly of claim 8 wherein the tubular support maintains the flexible element first portion at the angle relative to the flexible element second portion throughout movement of the actuator.

15. The deflectable catheter assembly of claim 8 wherein the inner surface of the actuator lumen is a second tubular support.

16. A deflectable catheter assembly comprising:
a) a catheter body extending from a deflectable distal end to a proximal end, and the catheter body includes an actuator lumen;
b) a housing engaged to the proximal end of the catheter body;
c) a flexible element extending from the housing through the actuator lumen to the deflectable distal end, the deflectable distal end is deflected by selective loading of the flexible element between tensioned and compressed configurations;
d) an actuator movably coupled with the housing and connected to the flexible element;
e) a tubular support engaged around the flexible element and connected to the actuator, wherein the tubular support moves with the actuator, and the tubular support substantially constrains lateral movement of the flexible element;
f) wherein in the tensioned configuration, the actuator is moved proximally, the flexible element is loaded in tension and the deflectable distal end is deflected toward a first direction; and
g) wherein in the compressed configuration, the actuator is moved distally, the flexible element is loaded in compression, and the deflectable distal end is deflected toward a second direction, and
h) wherein the tubular support laterally braces the flexible element against buckling in both the tensioned and compressed configurations.

17. The deflectable catheter assembly of claim 16 wherein in the compressed configuration, an inner surface of the actuator lumen laterally braces a portion of the flexible element against buckling.

18. The deflectable catheter assembly of claim 17 wherein one or more of the inner surface of the actuator lumen or the tubular support continuously constrains the flexible element from lateral movement between the deflectable distal end and the actuator.

19. The deflectable catheter assembly of claim 16 wherein the flexible element extends out of the catheter body at an intermediate portion of the catheter body between the deflectable distal end and the proximal end.

20. The deflectable catheter assembly of claim 19 wherein the tubular support is slidably engaged with an inner surface of the actuator lumen adjacent the intermediate portion.

21. The deflectable catheter assembly of claim 20 wherein the inner surface of the actuator lumen is a second tubular support.

22. A deflectable catheter assembly comprising:
a) a catheter body extending from a deflectable distal end to a proximal end, and the catheter body includes an actuator lumen;
b) a housing engaged to the proximal end of the catheter body;
c) a flexible element extending out of the catheter body at an intermediate portion between the deflectable distal end and the proximal end and then through the actuator lumen to the deflectable distal end, wherein the deflectable distal end is deflected by pushing and pulling of the flexible element;
d) an actuator movably coupled with the housing and connected to the flexible element;
e) a tubular support engaged around the flexible element and connected to the actuator, the tubular support moves with the actuator, and the tubular support substantially constrains lateral movement of the flexible element; and
f) the tubular support is telescopically received and engaged with an inner surface of the actuator lumen, and the inner surface of the actuator lumen substantially constrains lateral movement of the tubular support and the flexible element.

23. The deflectable catheter assembly of claim 22 wherein the tubular support is slidably engaged with the inner surface of the actuator lumen adjacent the intermediate portion.

* * * * *